US00PP08360P

United States Patent [19]

Bull

[11] Patent Number: Plant 8,360

[45] Date of Patent: Aug. 31, 1993

[54] IMPATIENS PLANT NAMED SUSANNE

[76] Inventor: Norbert Bull, Gärtnersiedlung 2, 2351 Gönnebek, Fed. Rep. of Germany

[21] Appl. No.: 802,857

[22] Filed: Dec. 6, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

An Impatiens plant named Susanne characterized by its bright orange-red flowers, compact growth habit, very early flowering, medium size green foliage without variegation, and its adaptability to pot, patio or bedding plant culture.

2 Drawing Sheets

The present invention relates to a new and distinctive cultivar of Impatiens plant, botanically known as Impatiens, and referred to be the cultivar name Susanne. The new cultivar was developed by me through controlled breeding by crossing seed or female parent identified as Seedling No. 18 with male or pollen parent identified as Seedling No. 14. Both parents are unreleased and propriety lines.

Asexual reproduction of the new cultivar by the inventor by terminal or stem cuttings taken at Gönnebek, Federal Republic of Germany has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Orange-red flowers.
2. Compact growth habit.
3. Medium size, medium green foliage without variegation.
4. Floriferous habit.
5. Suitable for pot plant, patio or bedding plant culture.

Susanne has a main flower color similar to the flower color of the cultivar Selenia. However, Susanne has a better and more rapid growth habit and flowers much earlier than Selenia.

The accompanying colored photographs illustrate the overall appearance of this cultivar, showing the colors as true as it is reasonably possible to obtain in a colored reproduction of this type. The photo at the top of sheet 1 comprises a top perspective view of a potted plant of Susanne. The bottom photo on sheet 1 shows a single flower (top side), and top and bottom views of a typical leaf. The photograph on sheet 2 shows the upper side and under side of typical flowers, a partially open bud with attached spur, and the upper side and bottom side of typical leaves. Scales in centimeters are included to show the size of these parts.

The following is a detailed description of my new Impatiens cultivar based on plants produced under normal commercial practice at Gönnebek, Federal Republic of Germany.

Color references are made to The Royal Horticultural Society (R.H.S.) Colour Chart except where general terms of ordinary dictionary significance are used.

Parentage: Controlled cross between Bull Unnamed Seedling No. 18 (seed parent)×Bull Unnamed Seedling No. 14 (pollen parent).

Propagation:

*Type cutting.*—Stem 15–20 mm long will grow to 4–5 cm in 20 days.

*Time to initiate roots.*—8 days at 22° C. summer.

*Time to initiate roots.*—10 days at 20° C. winter.

*Rooting habit.*—Very good.

Plant description:

*Form.*—Symmetrically mounded, self-branching.

*Habit of growth.*—Compact growth habit. Eight (8) weeks after sticking stem cuttings in 12 cm pots, plant is approximately 34 cm in diameter and 34 cm in height, measured from top of pot.

Foliage description:

(1) *Size.*—Medium. Approximately 9 cm in length and 3 cm in width at point of maximum width.

(2) *Shape.*—Generally ovate, with acute to acuminate tip and acute base; see photos.

(3) *Margin.*—Mildly serrated.

(4) *Color.*—(a) Young foliage upper surface: Medium green, RHS 137A. (b) Under surface: Light green. (c) Mature foliage upper surface: 137A. (d) Under surface: Light green approximately 191B-C.

(5) *Veination.*—Red veins on under side (see photo).

(6) *Variegation.*—None.

Flowering description:

*Flowering habit.*—Flowers from leaf whorl in uniform manner.

*Natural flowering season.*—March until October.

*Flower buds.*—Typical; brown red in color.

*Flowers borne.*—On pedicels red-purple in color.

*Quantity of flowers.*—Very floriferous, with many bright orange-red flowers in bloom at same time (see photo). Flowers both mask the crown and occur above the leaf canopy.

*Spur.*—Downwardly curved from base of calyx, approximately 4–5 cm in length and red-purple in color.

*Longevity.*—Flowers are long lasting and non-fading.

Petals:

*Number of petals.*—Five (5).

*Shape.*—Generally heart-shaped (see photo).

*Color.*—Upper surface: 40A, with center eye of 53B. Color very uniform. Under surface: Same as for top side, only slightly lighter.

*Size of flower.*—Medium, approximately 5.5 cm. in diameter.

Reproductive organs:

*Stamens.*—Five (5).

*Anthers.*—Hooded, red-orange in color.

*Pollen color.*—White.

*Stigma.*—Five in number, yellow in color.

*Styles.*—Yellow in color.

*Ovary.*—5 in number, size 3–5 mm., brown-dark green in color.

Disease resistance: No disease problems noted to date.

I claim:

1. A new and distinct Impatiens plant named Susanne, as illustrated and described.

* * * * *

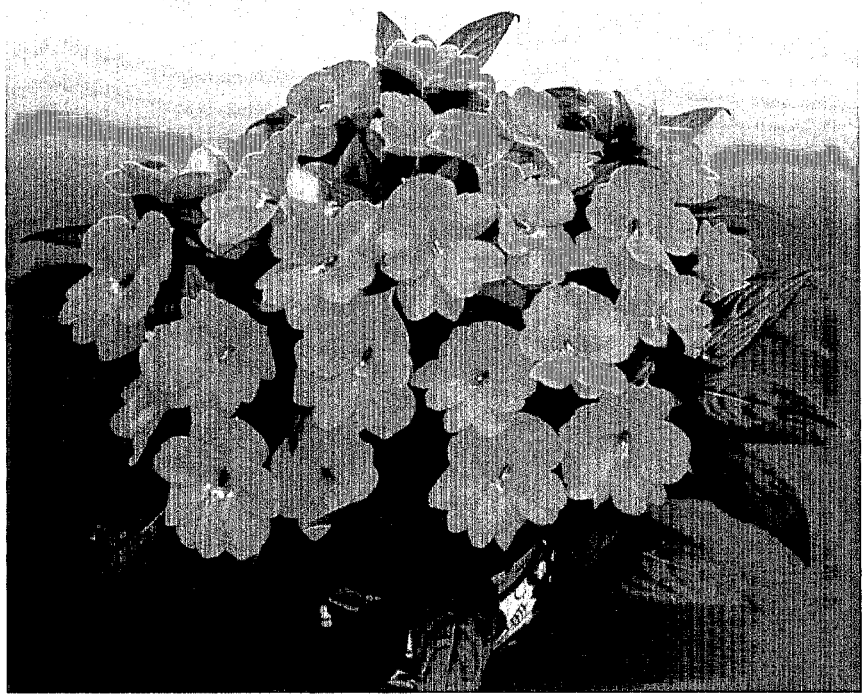
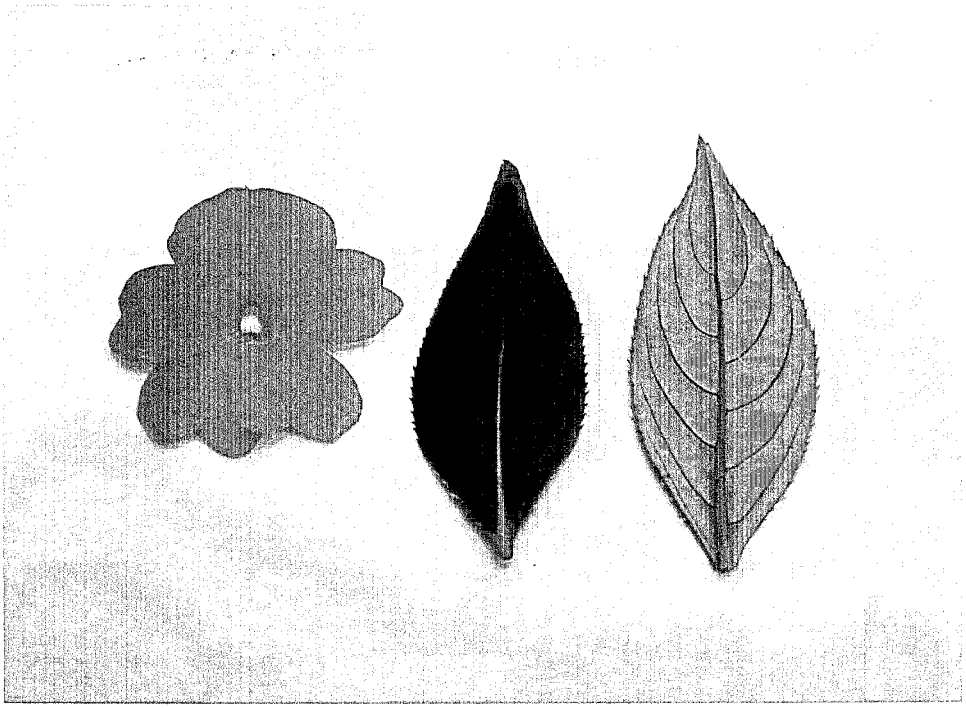

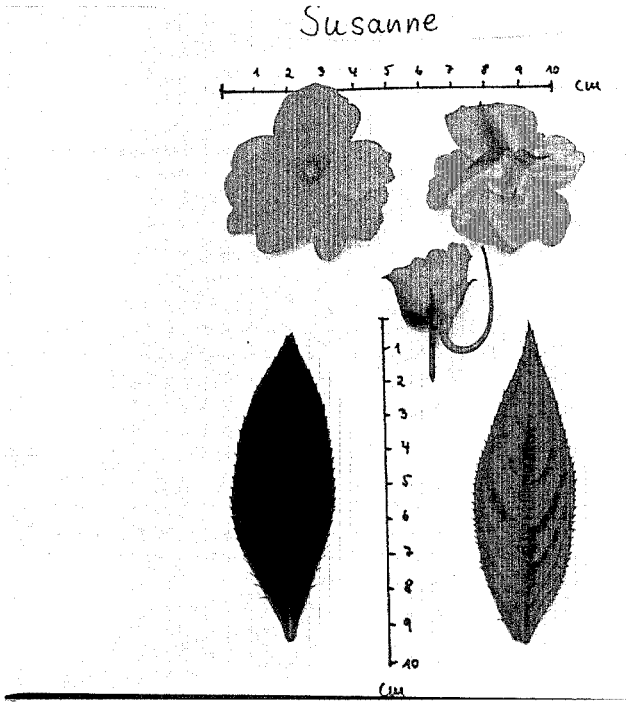
Susanne
1 2 3 4 5 6 7 8 9 10 cm
1 2 3 4 5 6 7 8 9 10
cm